(12) United States Patent
Quintero Barajas et al.

(10) Patent No.: US 10,000,435 B1
(45) Date of Patent: Jun. 19, 2018

(54) ENERGY AND ENVIRONMENTALLY INTEGRATED METHOD FOR PRODUCTION OF AROMATIC DICARBOXYLIC ACIDS BY OXIDATION

(71) Applicant: GRUPO PETROTEMEX, S.A. DE C.V., San Pedro Garza Garcia (MX)

(72) Inventors: José Gabriel Quintero Barajas, Altamira (MX); Pamela Shantal Ramírez Sosa, Altamira (MX); Alfredo Escobar López, Altamira (MX); Verona Medina Valencia, Cosoleacaque (MX); Arturo Bulbarela Croda, Cosoleacaque (MX); Bertha Morán Delgado, Cosoleacaque (MX)

(73) Assignee: GRUPO PETROTEMEX, S.A. DE C.V., San Pedro Garza Garcia (MX)

( * ) Notice: Subject to any disclaimer, the term of this patent is extended or adjusted under 35 U.S.C. 154(b) by 0 days. days.

(21) Appl. No.: 15/445,280

(22) Filed: Feb. 28, 2017

(51) Int. Cl.
    *C07C 51/265* (2006.01)
(52) U.S. Cl.
    CPC .................................. *C07C 51/265* (2013.01)
(58) Field of Classification Search
    CPC .................................................... C07C 51/265
    See application file for complete search history.

(56) References Cited

U.S. PATENT DOCUMENTS

| | | | |
|---|---|---|---|
| 7,355,068 B2 | 4/2008 | Wonders et al. | |
| 7,371,894 B2 | 5/2008 | Wonders et al. | |
| 7,568,361 B2 | 8/2009 | Wonders et al. | |
| 7,829,037 B2 | 11/2010 | Woodruff et al. | |
| 7,910,769 B2 | 3/2011 | Wonders et al. | |
| 8,501,986 B2 | 8/2013 | Wonders et al. | |
| 8,685,334 B2 | 4/2014 | Wonders et al. | |
| 8,790,601 B2 | 7/2014 | Shaikh et al. | |
| 2007/0244340 A1* | 10/2007 | Wonders | C07C 51/265 562/410 |
| 2010/0113826 A1* | 5/2010 | Fogle, III | C07C 51/265 562/408 |

* cited by examiner

*Primary Examiner* — Paul A Zucker
(74) *Attorney, Agent, or Firm* — Oblon, McClelland, Maier & Neustadt, L.L.P.

(57) ABSTRACT

A continuous process for oxidizing a di-alkyl substituted aromatic compound with compressed air in a primary bubble column reactor; including removing a portion of the three phase reaction medium to a post-oxidation bubble column unit supplied with compressed air separating the post oxidation reaction medium to an overhead gas and an underflow slurry; collecting overhead gases from the oxidation reactors and the de-gassing unit and conducting the combined overhead gases to a water removal column (WRC); transferring the underflow slurry from the de-gassing unit to a digestion unit to effect further oxidation without addition of air to the digestion unit; removing overhead gases to the water removal column; crystallizing the final oxidation slurry; and filtering the slurry on a rotary pressure filter; wherein a portion of the energy of the off gas from the WRC is employed to drive an air compressor to supply the compressed air for oxidation.

14 Claims, 12 Drawing Sheets

ENERGY AND ENVIRONMENTALLY INTEGRATED METHOD FOR PRODUCTION OF AROMATIC DICARBOXYLIC ACIDS BY OXIDATION

FIELD OF THE INVENTION

This invention relates to an energy efficient system and method to produce aromatic dicarboxylic acids by liquid phase oxidation of dialkyl-substituted aromatic compounds which collects and recycles catalysts and reactants to prepare aromatic dicarboxylic acids in a manner safe for the environment. Elements of the system and thus the method may be retrofit into existing chemical plants to obtain increased energy and production efficiency while yielding product of high quality.

BACKGROUND OF THE INVENTION

Liquid-phase oxidation reactions are commonly employed for the oxidation of aldehydes to acids (e.g., propionaldehyde to propionic acid), the oxidation of cyclohexane to adipic acid, and the oxidation of alkyl aromatics to alcohols, acids, or diacids. One important example of the oxidation of alkyl aromatics is the liquid-phase catalytic oxidation of para-xylene to terephthalic acid which is a feedstock in the production of polyethylene terephthalate ("PET"). PET is a well-known plastic used in great quantities around the world to make products such as bottles, fibers, and packaging.

In a liquid-phase oxidation process, a liquid-phase feed stream and a gas-phase oxidant stream are introduced into a reactor and form a multi-phase reaction medium in the reactor. The liquid-phase feed stream introduced into the reactor contains at least one oxidizable organic compound, while the gas-phase oxidant stream contains molecular oxygen. At least a portion of the molecular oxygen introduced into the reactor as a gas dissolves into the liquid phase of the reaction medium to provide oxygen availability for the liquid-phase reaction. If the liquid phase of the multi-phase reaction medium contains an insufficient concentration of molecular oxygen (i.e., if certain portions of the reaction medium are "oxygen-starved"), undesirable side-reactions can generate impurities and/or the intended reactions can be retarded in rate.

If the liquid phase of the reaction medium contains too little of the oxidizable compound, the rate of reaction may be undesirably slow. Further, if the liquid phase of the reaction medium contains an excess concentration of the oxidizable compound, additional undesirable side-reactions can generate impurities. Therefore, in order to obtain product of high purity at minimum cost much effort is expended to achieve efficient utilization of raw materials, including recycle of raw materials, minimum energy consumption and minimal waste treatment cost.

In order to obtain uniform distribution of the multi-phase oxidation reaction medium liquid-phase oxidation reactors may be equipped with agitation means to promote dissolution of molecular oxygen into the liquid phase of the reaction medium, maintain relatively uniform concentrations of dissolved oxygen in the liquid phase of the reaction medium, and maintain relatively uniform concentrations of the oxidizable organic compound.

Thus, agitation of the reaction medium may be provided by mechanical agitation as provided in continuous stirred tank reactors ("CSTRs"). However, CSTRs have a relatively high capital cost due to their requirement for expensive motors, fluid-sealed bearings and drive shafts, and/or complex stirring mechanisms. Further, the rotating and/or oscillating mechanical components of conventional CSTRs require regular maintenance. The labor and shutdown time associated with such maintenance adds to the operating cost of CSTRs. However, even with regular maintenance, the mechanical agitation systems employed in CSTRs are prone to mechanical failure and may require replacement over relatively short periods of time.

Bubble column reactors provide agitation of the reaction medium without requiring expensive and unreliable mechanical equipment. Bubble column reactors typically include an elongated upright reaction zone within which the reaction medium is contained. Agitation of the reaction medium in the reaction zone is provided primarily by the natural buoyancy of gas bubbles rising through the liquid phase of the reaction medium. This natural-buoyancy agitation provided in bubble column reactors reduces capital and maintenance costs relative to mechanically agitated reactors. Further, the substantial absence of moving mechanical parts associated with bubble column reactors provide an oxidation system that is less prone to mechanical failure than mechanically agitated reactors.

The efficient manufacture of high volume oxidation products of interest, such as terephthalic acid involves not only the oxidation process but also the work-up and isolation of the product and multiple unit operations conducted in series or in parallel are often employed in the total manufacturing process. Each of these operations may require energy input or may be a source of energy which may be captured and utilized. Further, control of reaction variables and reactant stoichiometry to optimize product yield and purity while minimizing waste and environmental impact may be key to obtaining commercial success in the operation.

Terephthalic acid is conventionally produced by liquid-phase oxidation of para-xylene. In a typical process, a solvent liquid-phase feed stream and a gas-phase oxidant stream are introduced into a primary oxidation reactor with a catalyst system and form a multi-phase reaction medium in the reactor. The solvent present in the liquid-phase generally comprises a low molecular weight organic acid such as acetic acid and water. In production systems wherein the solvent is recycled, the solvent may contain small quantities of impurities such as, for example, para-tolualdehyde, terephthaldehyde, 4-carboxybenzaldehyde (4-CBA), benzoic acid, para-toluic acid, para-toluic aldehyde (4-methylbenzaldehyde), alpha-bromo-para-toluic acid, isophthalic acid, phthalic acid, trimellitic acid, polyaromatics, and/or suspended particulate.

The catalyst is a homogeneous, liquid-phase system comprising cobalt, bromine, and manganese.

As described above, the use of bubble column reactors for the primary oxidation reaction offers many advantages over conventional continuous stirred tank reactors, and oxidation processes employing bubble column reactors are disclosed, for example, in U.S. Pat. No. 7,355,068, U.S. Pat. No. 7,371,894, U.S. Pat. No. 7,568,361, U.S. Pat. No. 7,829,037, U.S. Pat. No. 7,910,769, U.S. Pat. No. 8,501,986, U.S. Pat. No. 8,685,334 and U.S. Pat. No. 8,790,601, the contents of which are hereby incorporated by reference. Bubble column reactors typically include an elongated upright reaction zone within which the reaction medium is contained and agitation of the reaction medium in the reaction zone is provided primarily by the natural buoyancy of gas bubbles rising through the liquid phase of the reaction medium. This natural-buoyancy agitation provided in bubble column reactors reduces utility power, capital, and maintenance costs relative to mechanically agitated reactors.

The initial oxidation reactor system may include both a primary oxidation reactor providing principally for oxidizing the majority of the liquid phase oxidizable compound and optionally at least one secondary oxidation reactor. The principal objective of this secondary oxidation, which is also referred to as Post Oxidation or as Early Oxidative Digestion as in U.S. Pat. No. 7,393,973 (hereby incorporated by reference in its entirety), is to oxidize a substantial fraction of the liquid phase aromatic oxidation intermediates from primary oxidation onwards to TPA before entering the more severe oxidation conditions of digestion. This provides a useful reduction in the total amount of over-oxidation to carbon oxides incurred subsequent to primary oxidation.

The product withdrawn from the primary oxidation system is typically a slurry comprising a particulate solid-phase of crude terephthalic acid (CTA) and a mother liquor. CTA contains relatively high levels of impurities (e.g., 4-carboxybenzaldehyde, para-toluic acid, fluorenones, and other color bodies) that render it unsuitable as a feedstock for the production of PET. Thus, the CTA is typically subjected to a purification process that converts the CTA particles into purified terephthalic acid (PTA) particles that may be suitable for production of polyethylene terephthalate. The further purification of CTA may include an oxidative digestion treatment subsequently followed by a hydrogenation treatment.

Typically a slurry of CTA particles in a mother liquor obtained from the primary oxidation system may contain from about 10 to about 50 weight percent solid CTA particles, with the balance being mainly the acetic acid mother liquor. The solid CTA particles present in the initial slurry withdrawn from primary oxidation system may contain from about 400 ppmw to about 15,000 ppmw of 4-carboxybenzaldehyde (4-CBA).

CTA may be converted to PTA by oxidative digestion treatment in a series of additional oxidation reactors commonly referred to as "digesters" wherein further oxidation reaction is conducted at slightly to significantly higher temperatures than were used in the primary and secondary oxidation reactors. Optionally, the slurry of CTA particles may be subjected to a solvent replacement step before proceeding to the digester units, whereby the replaced solvent has reduced concentrations of aromatic impurities and/or altered concentrations of catalyst and water that are readjusted to be more suitable for oxidation catalysis in the digester units. Optionally, the mass fraction of solids in the CTA slurry may also be adjusted, with or without solvent replacement, prior to entering the digester units.

In order to make the precipitated oxidation intermediate impurities available for oxidation in the series of digesters, the particles are exposed to higher temperatures than in the primary oxidation to at least partially dissolve the CTA particles and expose the impurities to liquid-phase oxidation comprising additional molecular oxygen injected into the digester. The high surface area, crystalline imperfections, and super-equilibrium impurity concentrations of the small CTA particles are favorable, both kinetically and thermodynamically, for partial dissolution and on-going recrystallization of the terephthalic acid when the CTA slurry temperature is raised moderately above the temperature at which the CTA was formed in the primary oxidation.

The further oxidation conducted in the digester system is intended to reduce the concentration of 4-CBA in the CTA particles. The digestion temperature may be from 5° C. to about 90° C. higher than the primary oxidation temperature and typically may be from about 150° C. to about 280° C.

In a second effect of the digestion process, the terephthalic acid particles may experience Ostwald ripening which tends to provide larger particles having a narrowed particle size distribution in comparison to the CTA particles in the outlet stream of the primary oxidation.

In a third effect of the digestion process, the recrystallized terephthalic acid particles comprise reduced concentrations of many of the impurities that are resistant to catalytic oxidative correction to form terephthalic acid, impurities such as polyaromatic carboxylic acid species, notably including many colored species such as 2,6-DCF and 2,7-DCF, inter alia. This reduction is caused by a closer approach to equilibrium distribution of the oxidation resistant impurities between solid and liquid phases, resulting from both the hotter operating temperature than in initial oxidation and also to the extended recrystallization time during the digestion process. The reduction in solid phase concentration of oxidation resistant impurities is further enhanced if the optional solvent replacement step has used a relatively more pure solvent such as, for example, distilled aqueous acetic acid from a solvent dehydration process used for removing the water produced by oxidation of the para-xylene.

Following the digestion treatment the purified product from the oxidative digestion may be crystallized and collected in one or more crystallization units and isolated by filtration to a mother liquor filtrate and a filter cake. The filtercake is extensively washed with solvent to remove catalyst and other impurities including methyl acetate formed during the oxidation processes.

The filtercake may then be blown free of retained wash and mother liquor and dried in an oven system to remove residual solvent.

A conventional hydrogenation process may then be employed for further purification. The dried washed filtercake is reslurried in water and catalytically hydrogenated to convert impurities to more desirable and/or easily-separable compounds.

The terephthalic acid may be selectively precipitated from the hydrogenated solution via multiple crystallization steps, and isolated.

The multiple systems required for primary oxidation, digestion, crystallization, filtration, drying and purification require energy management for thermal control of the various operations, overhead systems to manage exhaust vapors from the oxidation and digestion systems, a supply of air oxidant and systems to collect and recycle solvent and catalyst. Thus there is a need to further integrate existing liquid-phase oxidation systems for oxidation of dialkyl aromatic compounds to reduce total energy requirements while maximizing production efficiency and product yield. There is a further need to develop new liquid phase oxidation systems which provide efficient energy management, materials recycle and waste minimization in comparison to existing technology.

SUMMARY OF THE INVENTION

Therefore, one object of the present invention is to provide methods to integrate energy and materials management in existing liquid phase oxidation systems for dialkyl aromatic compounds to provide overall reduced energy consumption and significantly improved production efficiency.

Another object of the present invention is to provide a new method and system for liquid phase oxidation systems for dialkyl aromatic compounds having significantly reduced energy consumption and significantly improved production efficiency in comparison to conventional systems.

These and other objects are provided by the present invention, the first embodiment of which provides a continuous process to prepare an aromatic dicarboxylic acid, comprising:

oxidizing a di-alkyl substituted aromatic compound with compressed air in an acetic acid reaction medium in a primary bubble column reactor in the presence of a catalyst;

removing a portion of the three phase reaction medium containing catalyst from the primary bubble column reactor to a post-oxidation bubble column unit supplied with compressed air;

transferring the post oxidized reaction medium to a de-gassing unit and separating the post oxidation reaction medium to an overhead gas and an underflow slurry;

collecting an overhead gas from each of the primary oxidation reactor and the post-oxidation reactor with the overhead gas from the de-gassing unit and conducting the combined overhead gases to a water removal column;

transferring the underflow slurry from the de-gassing unit to a digestion unit, wherein the temperature of the underflow slurry is increased to a temperature to at least partially dissolve precipitated solids and effect further oxidation of exposed intermediate oxidation products with air and catalyst present in the underflow slurry, to obtain a final oxidation slurry;

removing overhead gases from the digestion unit to the water removal column;

crystallizing the final oxidation slurry to obtain a filtration-ready slurry of the aromatic dicarboxylic acid;

filtering the filtration-ready slurry on a rotary pressure filter to obtain a mother liquor filtrate and a filtercake;

wherein the overhead gases sent to the water removal column are separated in the water removal column to an off gas comprising steam removed from the top of the column and an underflow liquid comprising acetic acid, at least a portion of the energy of the off gas comprising steam is collected and employed to drive an air compressor to supply the compressed air to the bubble column primary reactor and the post-oxidation bubble column unit, and a water content of the continuous oxidation is controlled by removal of water condensed from the water removal column off-gas.

In a further aspect, the first embodiment may include washing the filtercake with acetic acid;

flowing nitrogen gas through the acetic acid washed filtercake to obtain a solid filtercake;

drying the solid filtercake to remove solvent;

reslurrying and purifying the dried filtercake of the aromatic dicarboxylic acid in an aqueous medium to obtain a purified dicarboxylic acid slurry;

filtering the purified aqueous slurry in a rotary pressure filter to obtain a final filtercake of the aromatic dicarboxylic acid and an aqueous mother liquor filtrate;

membrane filtering the aqueous mother liquor filtrate to obtain a water permeate; and transferring the water permeate to the water removal column.

In another aspect, the first embodiment may include:

reslurrying the dried filtercake of the aromatic dicarboxylic acid in an aqueous medium;

treating the aqueous slurry with hydrogen in the presence of a hydrogenation catalyst to obtain a crystallization ready aromatic dicarboxylic acid slurry;

crystallizing the aromatic dicarboxylic acid in a series of at least two crystallization units;

filtering the crystallized aqueous slurry in a rotary pressure filter to obtain a final filtercake of the aromatic dicarboxylic acid and an aqueous mother liquor filtrate:

membrane filtering the aqueous mother liquor filtrate to obtain a water permeate; and transferring the water permeate to the water removal column as a water reflux.

In a second embodiment the continuous oxidation process of the invention further comprises:

washing the filtercake with water to remove solvent and catalyst;

flowing nitrogen gas through the water washed filtercake to obtain a solid filtercake;

reslurrying and purifying the solid filtercake of the aromatic dicarboxylic acid in an aqueous medium to obtain a purified aromatic dicarboxylic acid slurry;

filtering the purified aqueous slurry in a rotary pressure filter to obtain a final filtercake of the aromatic dicarboxylic acid and an aqueous mother liquor filtrate;

membrane filtering the aqueous mother liquor filtrate to obtain a water permeate; and transferring the water permeate to the water removal column.

In a further version of the second embodiment reslurrying and purifying the dried filtercake of the dicarboxylic acid comprises:

reslurrying the solid filtercake of the aromatic dicarboxylic acid in an aqueous medium;

treating the aqueous slurry with hydrogen in the presence of a hydrogenation catalyst to obtain a crystallization ready aromatic dicarboxylic acid slurry;

crystallizing the aromatic dicarboxylic acid in a crystallization unit;

filtering the crystallized aqueous slurry in a rotary pressure filter to obtain a final filtercake of the aromatic dicarboxylic acid and an aqueous mother liquor filtrate;

membrane filtering the aqueous mother liquor filtrate to obtain a water permeate; and transferring the water permeate to the water removal column for as a water reflux.

In particular versions of all the above embodiments and aspects thereof, the di-alkyl substituted aromatic compound is para-xylene and the aromatic dicarboxylic acid is terephthalic acid.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

As described above, the present invention is directed to energy and materials recycle integration in an industrial scale continuous liquid-phase oxidation of di-alkyl substituted aromatic compounds to a corresponding aromatic dicarboxylic acid. The process to be described in detail in the following paragraphs describes the liquid phase oxidation of para-xylene (PX) to terephthalic acid (PTA) and the description references various intermediates and impurities associated with the specific chemistry of PTA manufacture. However, the general integrated energy management and recycle systems associated with the continuous PX oxidation process is applicable to the oxidation of any di-alkyl substituted aromatic compound.

Throughout the following description the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted. All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

When numerical contents are described, the units are percent by weight or ppm by weight unless otherwise specified. The terms lowermost and uppermost when applied to describe location within a reactor designate an upper 10% and lower 10% of a total height of the reaction mixture within the reactor.

The integrated oxidation, material recycle and energy management systems according to the various embodiments of the present invention will be described with reference to the associated Figures. It must be understood that the figures are schematic and show arrangement and interaction of the systems and unit operations employed. The actual spatial positioning and locations of the systems may vary greatly depending on the physical structure of the facility of manufacture and whether an existing system is retrofitted or a new system constructed.

Figure 1:
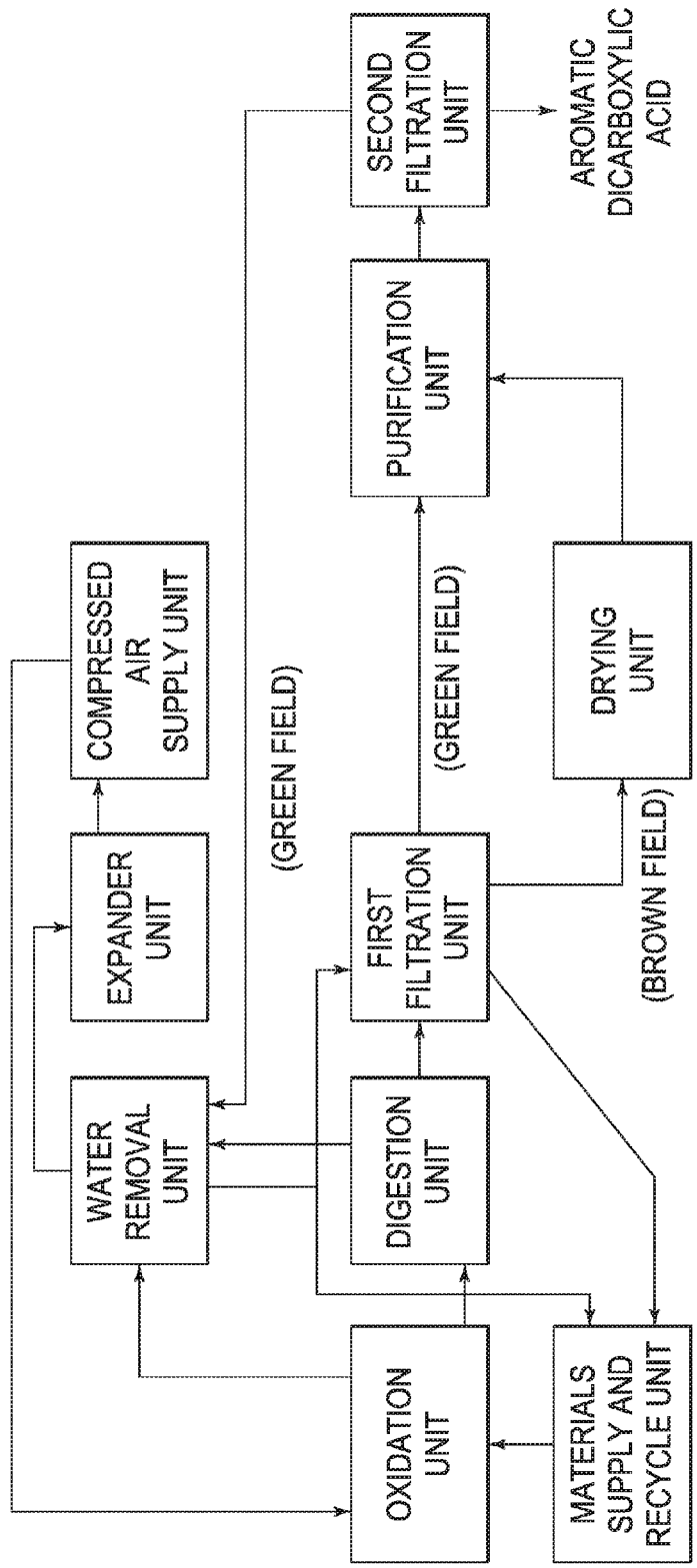
FIG. 1 shows a schematic diagram of the unit systems employed in the process according to various embodiments of the invention.

An integrated oxidation unit system according to an embodiment of the invention is shown in FIG. 1 and as indicated, includes a materials supply and recycle unit, an oxidation unit, a water removal unit, an expander unit, a compressed air supply unit, a digestion unit, a crystallizer unit a first filtration unit, an optional drying unit, a purification unit, a second filtration unit and a filtrate treatment unit. As understood by one of skill in the art the total system may include other auxiliary units to support and control the integration and performance of the described units and the invention is not intended to be limited to the units shown in FIG. 1.

Each of the unit systems will be described in reference to the appropriate Figure.

Figure 2:
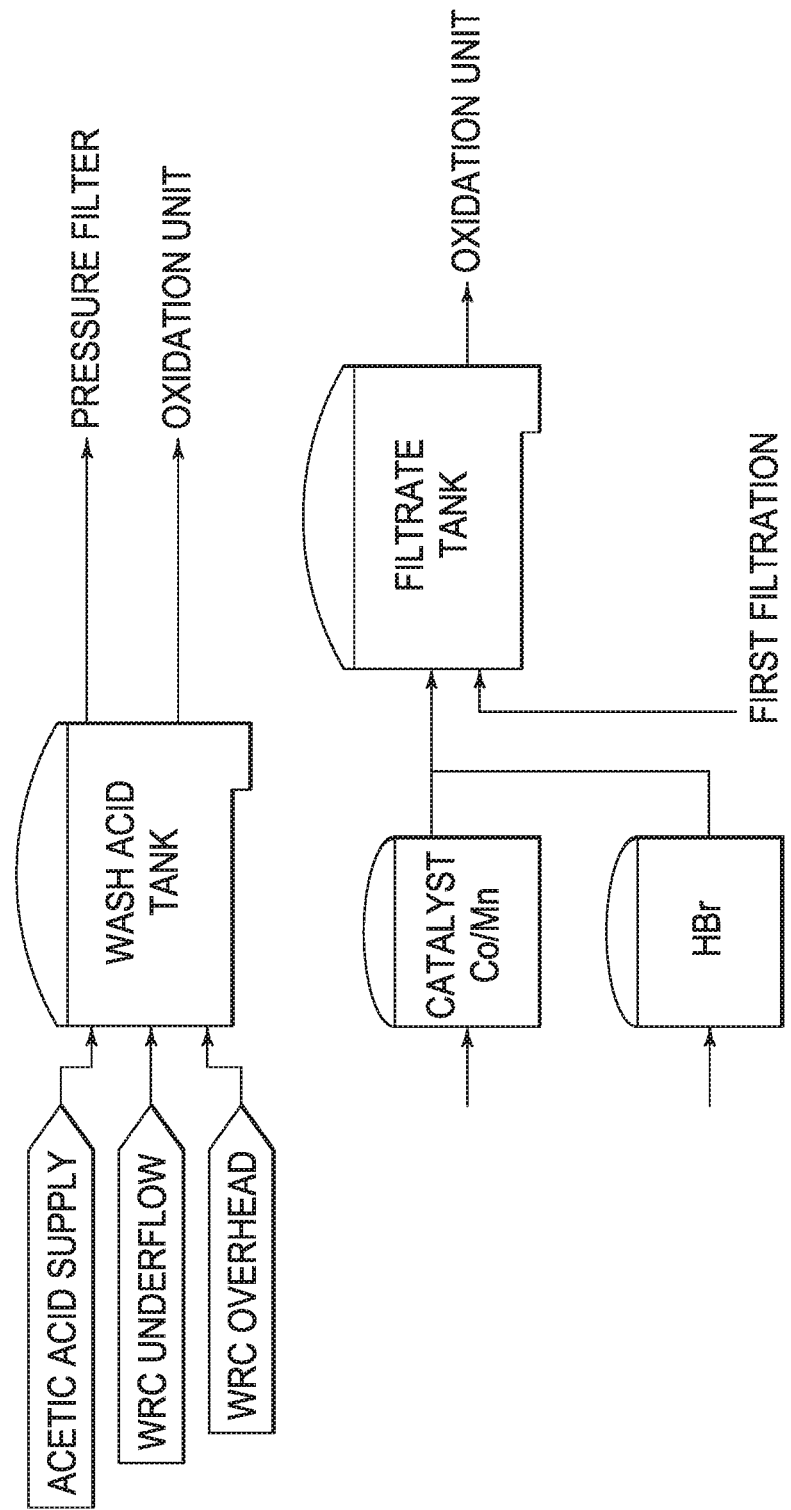
FIG. 2 shows a schematic diagrammatic arrangement of the Materials Supply and Recycle unit according to one embodiment of the invention.

FIG. 2 shows the material supply unit which contains as main components, a wash acid tank, a filtrate tank, a catalyst tank containing Co/Mn catalyst and a HBr supply tank.

The wash acid tank serves as the main collection point of the system to recycle the acetic acid from multiple sources as described in the following description. However, a main source of recycled acetic acid is from the underflow (2) of the water removal column (WRC). The wash acid tank also serves to collect solids-free and catalyst-free acid from vent condensers and vacuum systems (not shown in FIG. 2). Fresh acetic acid may be added to this tank from an associated storage supply (1) in order to maintain a sufficient level of acetic acid to support the multiple uses of acetic acid in the total integrated system. It is preferred to prevent contamination of this tank with solids or catalyst.

Wash acid may be provided for wash to the primary product filters (Brownfield) described below.

Acetic acid from the wash acid tank may be supplied to the top of the primary oxidation reactor as spray reflux to prevent solid carry-over in the off-gas vent (FIG. 3) and to promote separation of water as an acetic acid/water vapor to the off-gas vent system. A small amount of acetic acid is also supplied to the compressed air lines feeding air to the primary oxidizer and secondary oxidizer to wash the lines free of solids (not shown).

Acetic acid from the wash acid tank is also supplied to the filtrate tank. The filtrate tank is a collection vessel for recycle streams containing catalyst and/or solids and is supplied with cobalt, manganese and hydrogen bromide (HBr) coming from associated catalyst supply tanks.

Figure 9:
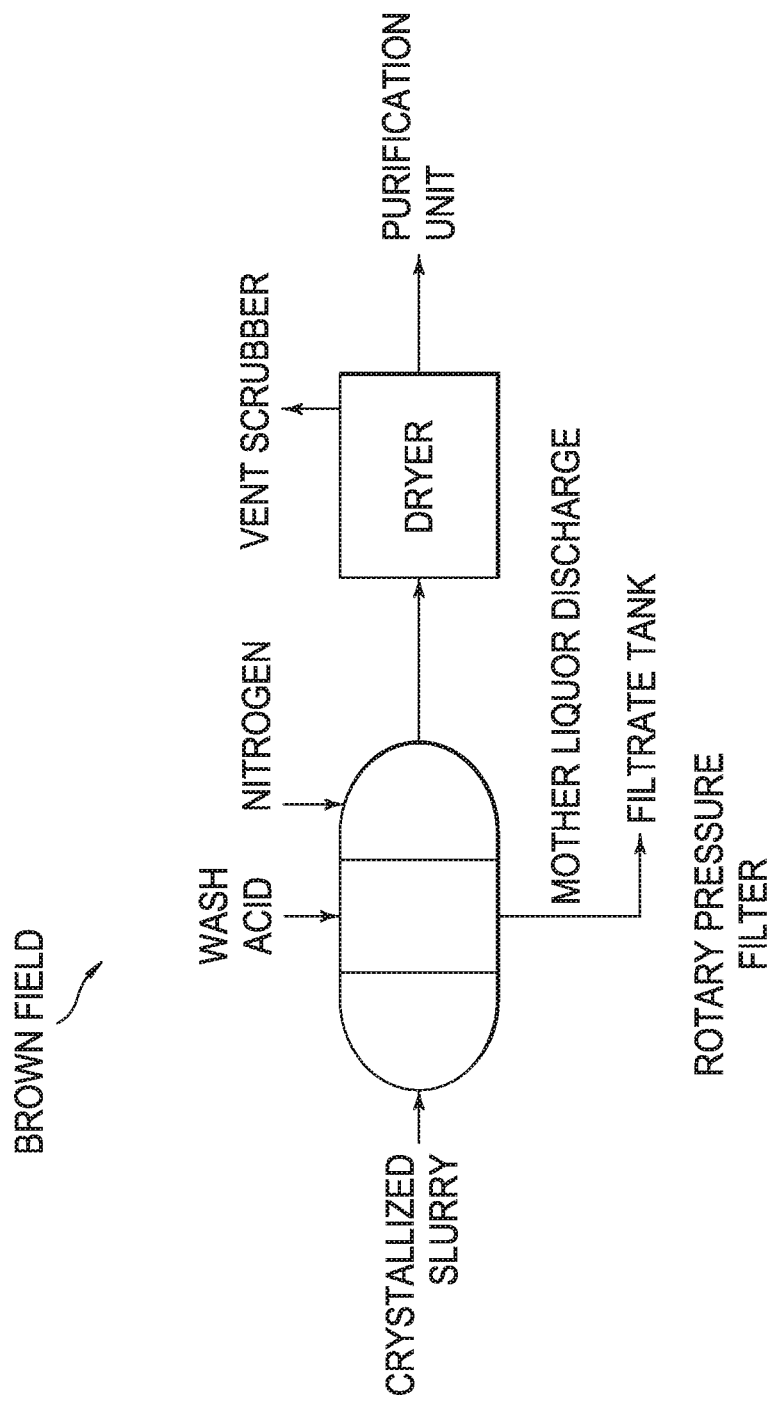
FIG. 9 shows a schematic diagrammatic arrangement of the First Filtration unit according to one embodiment of the invention (Brownfield).

Acetic acid from the Wash Acid Tank may also be employed as a wash of the filtercake in the rotary pressure filter of the first filtration unit (FIG. 9).

As indicated, filtrate containing acetic acid, water cobalt, manganese and bromine, as well as any other acetic acid streams containing solids are recycled and collected in the filtrate tank.

The catalyst is a homogeneous, liquid-phase system comprising cobalt, bromine, and manganese. The concentration of catalyst in the system may be controlled by monitoring component concentrations at defined points and making adjustments when appropriate. Such monitoring and control is understood by persons of skill in the technology.

The acetic acid concentration of the filtrate catalyst mixture fed to the primary oxidation reactor may be from 83 to 96 wt. % of the total filtrate feed weight, preferably 85 to 94 wt. % and most preferably, 88 to 93 wt. %.

The filtrate catalyst level is important for oxidation performance in terms of yield and quality. Excess catalyst is to be avoided because once catalyst is in the system; the loss rate may be comparatively low and may quickly get out of control.

Throughout the system filtrate and wash acid tanks are connected to a process vent scrubber (not shown) which recovers and recycles acetic acid from the vapor streams before venting to the atmosphere.

Figure 3:
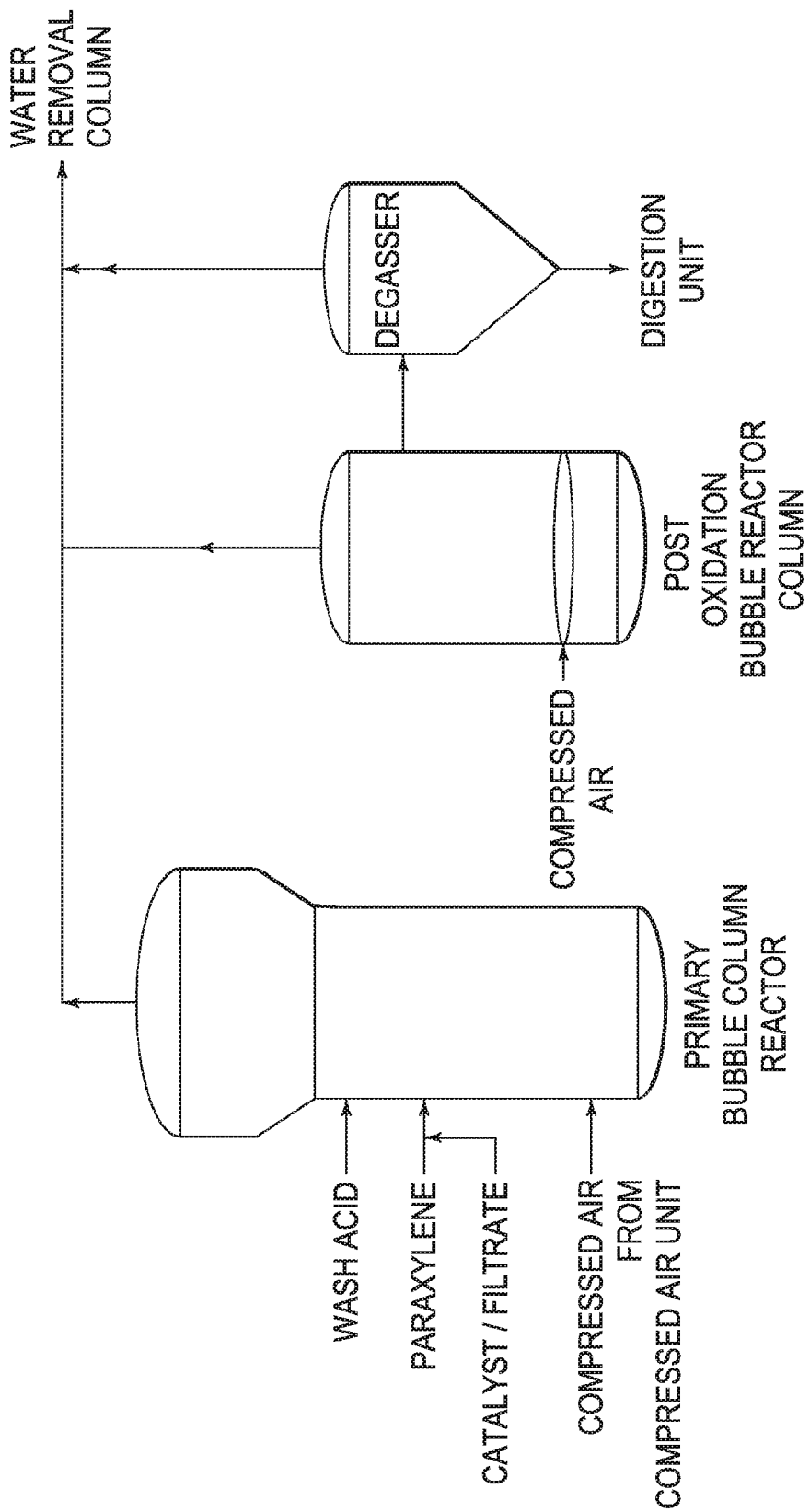
FIG. 3 shows a schematic diagrammatic arrangement of the Oxidation unit according to one embodiment of the invention.

The oxidation unit as shown in FIG. 3 contains a primary oxidation reactor, a secondary oxidation reactor and a degasser.

During the continuous liquid phase oxidation feeds of p-xylene, filtrate containing catalyst from the filtrate tank and air are fed to the primary oxidation reactor (FIG. 3). The compressed air supplied to the primary oxidation reaction mixture may be fed through an air sparger-ring located in a lowermost region of the primary oxidation reactor, preferably within a lowermost 10% of the total height of the reaction medium in the primary bubble column oxidation reactor. The compressed air supplies both the oxidant $O_2$ required for oxidation of the p-xylene and agitation of the reaction mixture in the column.

The time-averaged concentration of oxygen, on a dry basis, in the gaseous effluent discharged from the reactor via the gas outlet is preferably in the range of from about 0.5 to about 9 mole percent, more preferably in the range of from about 1 to about 7 mole percent, and most preferably in the range of from 1.5 to 5 mole percent.

The aerated reaction mixture may be essentially homogeneous and occupies approximately 60 to 98% w, preferably 80 to 96% w and most preferably 85 to 94% w of the total volume of the primary oxidation reactor.

The purity of the para-xylene fed to the primary oxidation reaction mixture may be 99.5% or greater, preferable 99.6% or greater and most preferable 99.7% or greater.

A recycled solution of relatively catalyst-free, weak acetic acid from the wash acid tank is fed through spray nozzles in the vapor head space as previously described. The reflux flow may be adjusted to control the total reaction volume in the primary oxidizer. Maintenance of the reflux stream may be useful to control the vapor stream to the water removal column described in the following paragraphs. Upsets in this stream can result in water removal column overload and possible damage to the off-gas treatment system also described in the following paragraphs.

The combination of temperature, pressure and catalyst levels produce a nearly complete conversion of p-xylene to terephthalic acid in the primary oxidation reaction mixture. Operating parameters for the primary oxidation include a temperature of 125 to 200° C., preferably 140 to 180° C. and most preferably 150 to 170° C.; a water content of 2 to 12% by weight, preferably, 2 to 16% by weight and most preferably approximately 3% by weight; a cobalt concentration of 300 to 6000 ppmw, preferably, 700 to 4200 ppmw and most preferably 1200 to 3000 ppmw; a manganese content of 20 to 1000 ppmw, preferably 40 to 500 ppmw and most preferably 50 to 200 ppmw; a bromine content of 300 to 5000 ppmw, preferably 600 to 4000 ppmw and most preferably, 900 to 3000 ppmw. A total solids content of the primary oxidation reaction mixture may be from 5 to 40 wt. %, preferably 10 to 35 wt % and most preferably 15 to 30 wt %.

A side-draw transfer pipe located in an uppermost portion of the primary oxidation reactor connects to the secondary oxidation reactor (post-oxidizer) and allows the aerated reaction mixture to flow into the post oxidizer where additional compressed air is fed via a bottom sparger-ring. The reaction mixture obtained within the uppermost primary oxidation reaction medium comprises a particulate solid-phase of crude terephthalic acid (CTA) and a mother liquor. CTA contains relatively high levels of impurities (e.g., 4-carboxybenzaldehyde, para-toluic acid, fluorenones, and other color bodies). The solid CTA particles present in the slurry entering the secondary oxidation reactor from the primary oxidation reactor may contain about 15,000 ppm of 4-carboxybenzaldehyde (4-CBA) and/or para-toluic acid.

Approximately 80 to 99% of the total compressed air supplied to the oxidation reaction medium of this invention is supplied to the primary oxidation reactor and the remaining approximately 1% to 20% to the post oxidizer. According to embodiments of the present invention compressed air or oxygen is not added to the system after the post oxidizer.

Operating in semi-plug flow fashion, the post oxidizer is responsible for reacting away the liquid phase p-toluic acid in the oxidizer reaction mixture.

The post oxidizer is connected to a degasser unit via a side draw transfer to a degasser unit and aerated slurry from the post oxidizer is separated in the degasser unit to a liquid slurry underflow and overhead gas.

The CTA in the underflow from the post oxidizer is relatively high in solid phase impurities such as 4-CBA. To reduce the impurity level further, it is necessary to elevate the temperature to re-dissolve crystals and react away the impurities, which is the purpose of the digestion system in the digestion unit as described below. Underflow slurry from the secondary oxidation reactor is transferred to the digestion system via the degasser and the overhead vapors are sent to the water removal unit as indicated in FIG. 3.

Figure 4:
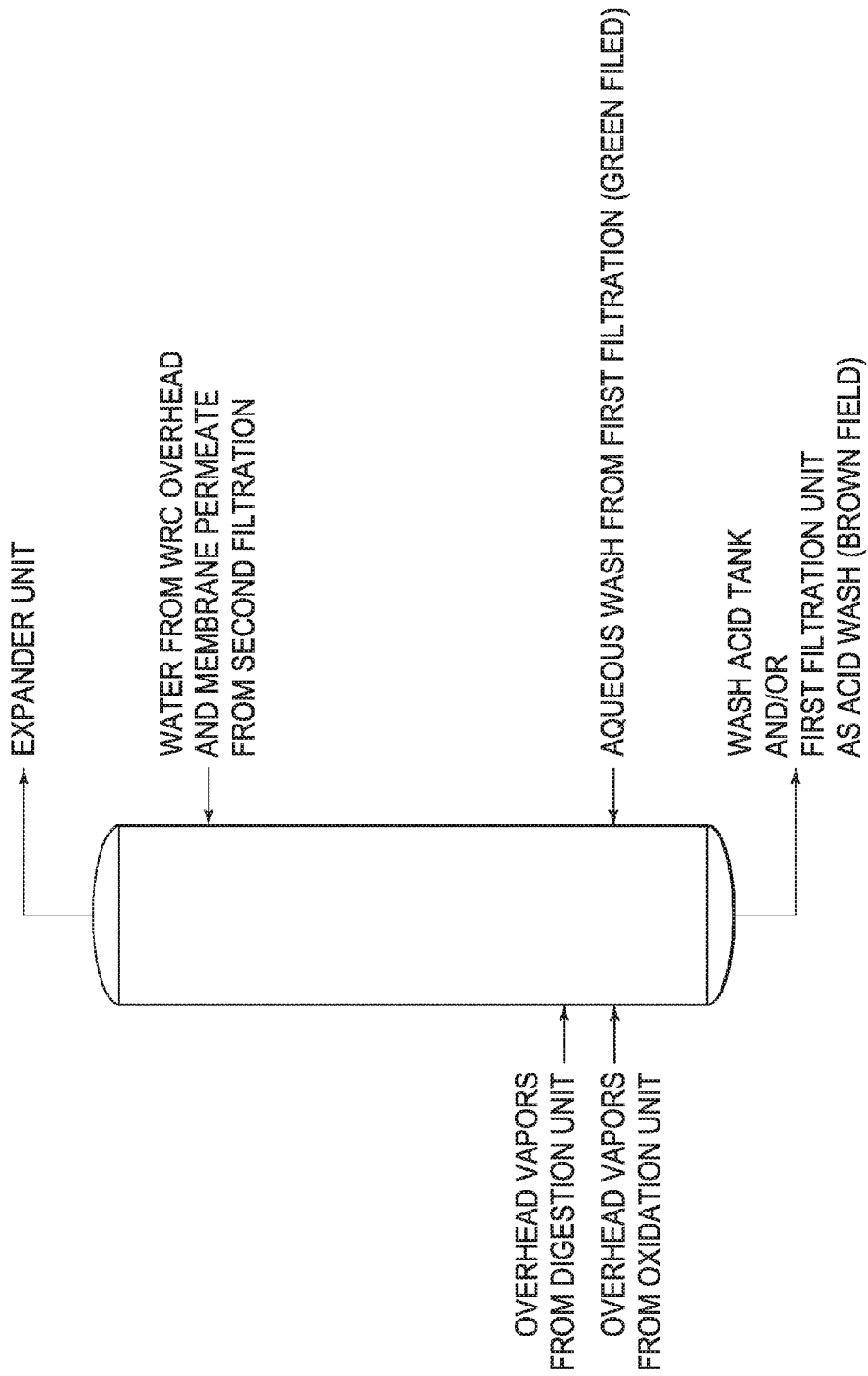
FIG. 4 shows a schematic diagrammatic arrangement of the Water Removal unit according to one embodiment of the invention.

The water removal unit as shown in FIG. 4 contains a water removal column.

The water removal column (WRC) provides the main method to remove water from the continuous process system and control water content of the oxidation reaction mixtures.

The oxidizer unit overhead gases from the primary oxidation reactor secondary reactor and degasser are sent to the water removal column. The WRC may be a distillation column equipped with trays and/or packing. The oxidation reactions of the primary oxidation and the secondary oxidation are exothermic and the generated heat vaporizes acetic acid, water and low boiling compounds from the reaction mixture slurry. This vapor, along with nitrogen, un-reacted oxygen and small amounts of carbon monoxide and carbon dioxide obtained as overhead vapor from each of the primary oxidizer, the post oxidizer and the degasser is introduced to the base of the water removal column. The overhead vapor has sufficient thermal energy to operate the water removal column.

In addition to receiving the overhead vapors from the oxidation unit, the WRC may also receive overhead vapors from the digestion unit and membrane water permeate from the membrane filter of the filtrate treatment unit.

The underflow from the water removal column may contain about 90% acetic acid and 10% water. The water content in the overall process is controlled at the base of this column. Part of the water column underflow may be pumped directly to the rotary pressure filters as an acetic acid wash of the filter cake.

The excess underflow not employed as wash for the filtercake may be sent through a series of steam generators or at least one steam generator (not shown), for power generation in compressor steam turbines. Following the steam generators, the underflow may be cooled in a cooling unit and sent to the wash acid tank for recycle back into the system as previously described.

The remaining thermal energy of underflow may be harvested in a series of one or more heat exchange units (not shown) in route to the wash acid tank.

Figure 5:
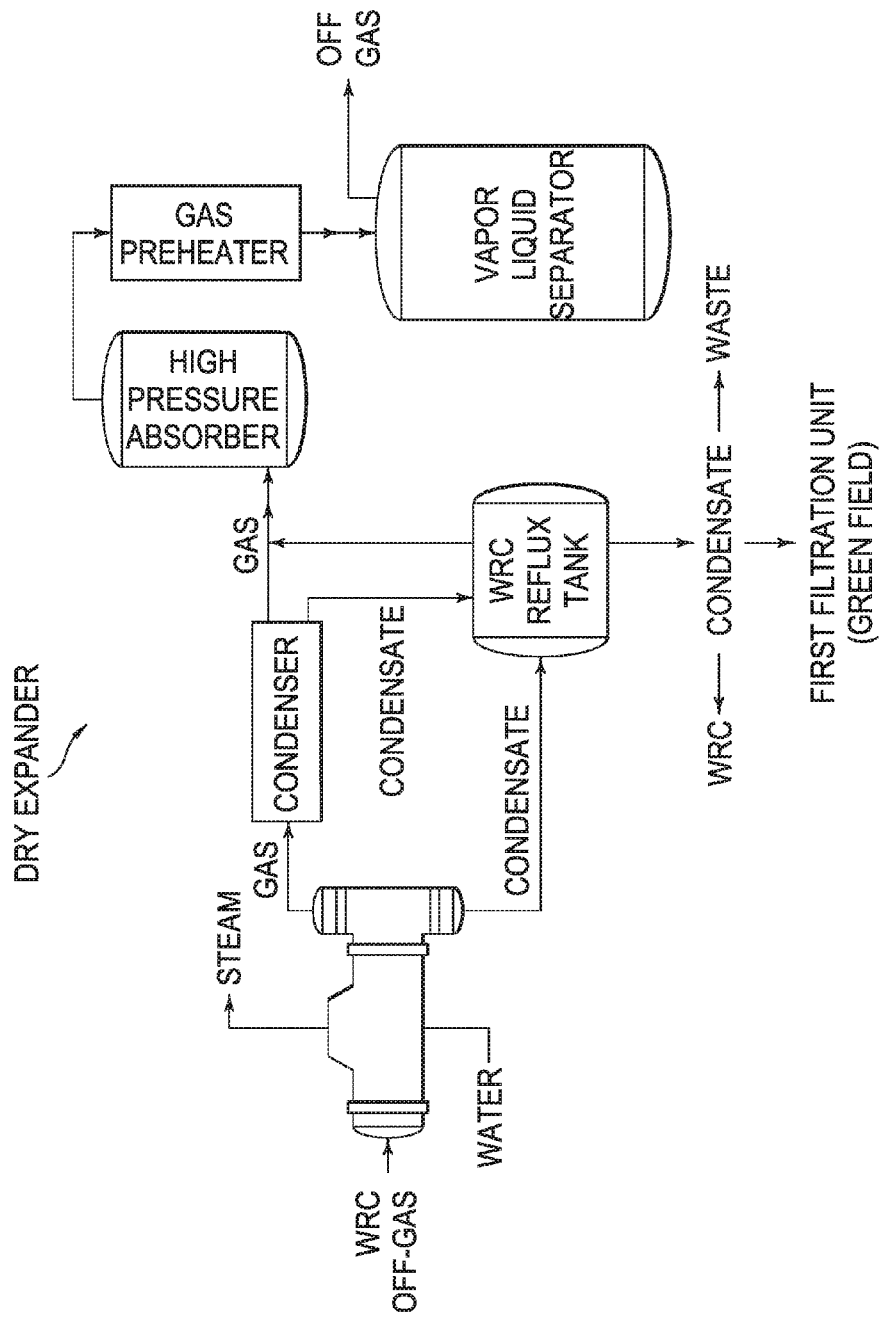
FIG. 5 shows a schematic diagrammatic arrangement of an Expander unit according to one embodiment of the invention (Dry Expander).

The water removal column off-gases may be sent through one or more steam generators to convert the vapor thermal energy to process steam as indicated in FIG. 5. Only one generator is shown in FIG. 1; however, multiple generators in series or in parallel may be included to generate process steam from the exothermic energy of the oxidation process. The vapors may then be partially condensed in the Condenser and both vapor and condensate collected in the WRC Reflux Tank where the non-condensed off gas and the condensate may be separated. The condensate from the overhead vapors collected at this stage contains about 99 wt % water with traces of acetic acid and methyl acetate and may be pumped back to the top of the water removal column as reflux or may be dumped as waste water to a waste sump.

The off gas is washed in a high pressure absorber (HPA) in order to recover any remaining para-xylene contained in the off gas stream. After the HPA the off gas is heated to 150 to 240° C., preferably 170 to 220° C. in one or more preheater units before being sent via a vapor-liquid expander to the off gas expander system of the compressed air unit where the energy contained in the stream is recovered by expansion and is used to move the compressor train.

Figure 6:
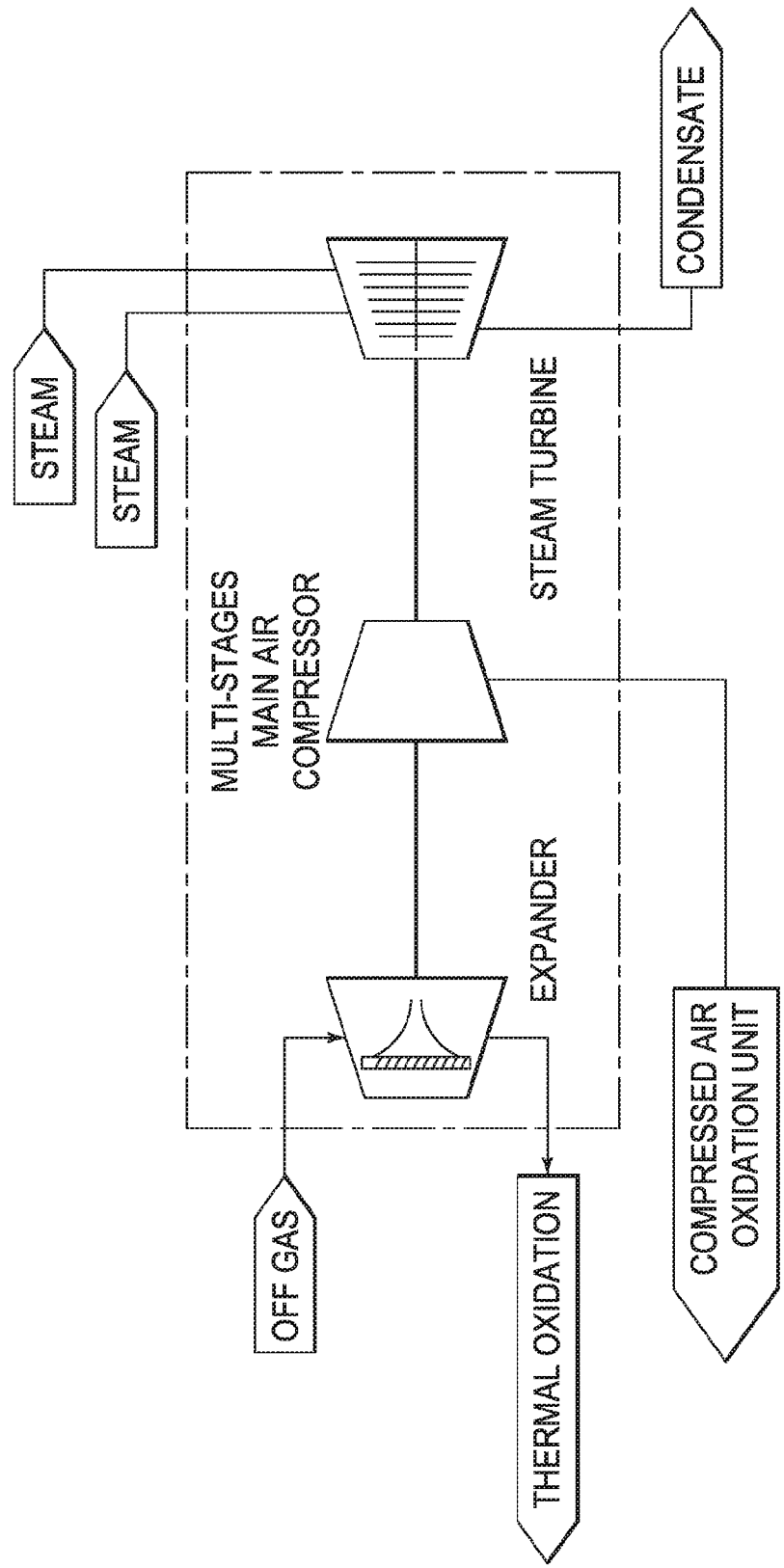
FIG. 6 shows a schematic diagrammatic arrangement of the Compressed air supply unit according to one embodiment of the invention.

FIG. 6 shows a schematic diagram of the compressed air unit.

The air compressor provides compressed process air to the primary oxidation reactor and the secondary oxidation reactor according to the reaction requirements as previously described. The air may be taken from the atmosphere through an inlet filter (not shown) and is compressed in a multi-stage air compressor. One of ordinary skill will recognize that compressor units of differing number of stages may be employed within the metes and bounds of the present invention. After each stage the compressed air is cooled with cooling water and the water condensed from the compressed air is separated in the inter-cooler heat exchangers. Normal operating conditions for the compressor are from 301.325 to 2401.33 kPaA, preferably 401.325 to 1601.33 kPaA and most preferably 601.325 to 1201.33 kPaA discharge pressure.

The power required to compress the air, is supplied by a steam turbine and the off gas expander receiving the preheated off gas from the HPA, both the steam turbine and the off gas expander being mounted on the same shaft with the compressor. The steam used in the steam turbine may be generated within the process including from the thermal energy of the overhead gas from the WRC as previously described and from the thermal energy of the underflow of the WRC during transfer to the wash acid tank as previously described.

Figure 7:
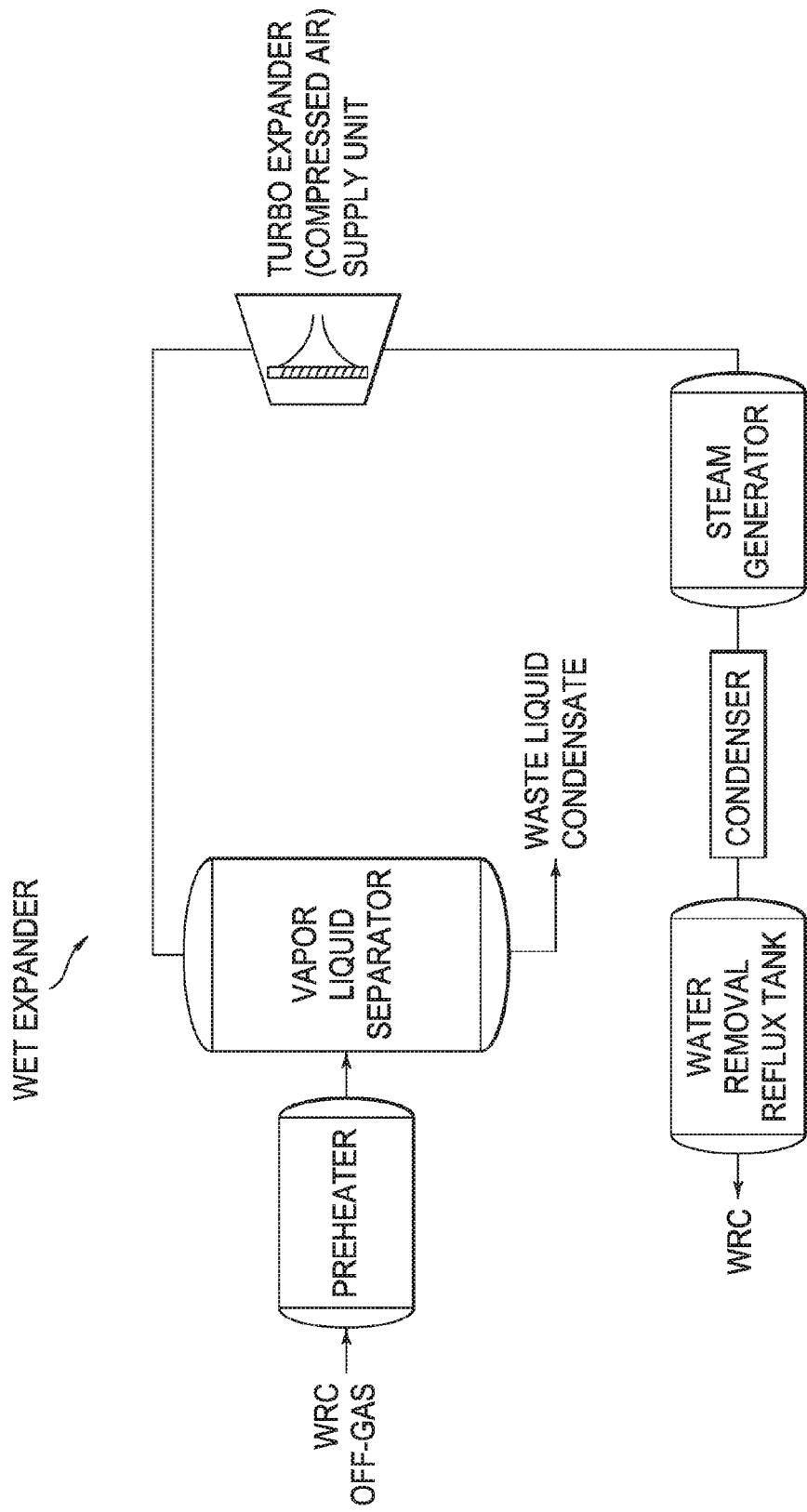
FIG. 7 shows a schematic diagrammatic arrangement of an alternative Expander unit according to one embodiment of the invention (Wet Expander).

In an alternative embodiment to the expander unit shown in FIG. 5 (dry expander), the WRC off gas may be processed as shown schematically in FIG. 7 (wet expander).

The hot overhead vapor exiting the water removal column is at its dew point. Condensation of this stream may result in the formation of bromhydric acid (HBr), which is highly corrosive. To avoid this problem and to efficiently recover and utilize the energy available in the off gas stream, the off gas stream from the WRC may be first superheated in one or more gas preheaters. The off gas preheater(s) may use either high pressure steam or any other heat transfer media. The superheated WRC off gas may be routed through a vapor-liquid expander to the compressed air unit off gas expander (turbo expander) shown in FIG. 6 to directly recover the energy contained in the superheated stream.

After exiting from the turbo expander, the off gas is sent to one or more steam generators to produce low pressure steam. Following the steam generator(s), all vapors are partially condensed in a condenser and collected in a water removal reflux tank. The water may then be returned to the WRC as reflux liquid.

The motor generator may be used in generator mode to produce electric energy from the remaining energy available during normal operation of the oxidation process. During compressor train start-up the motor-generator may be used as a drive motor.

In either the dry or wet expander embodiments the energy generated in the exothermic oxidation reaction in the oxidation unit is harvested and employed to at least drive the air compressor unit which supplies the compressed air for the primary and secondary oxidation reactors.

Figure 8:
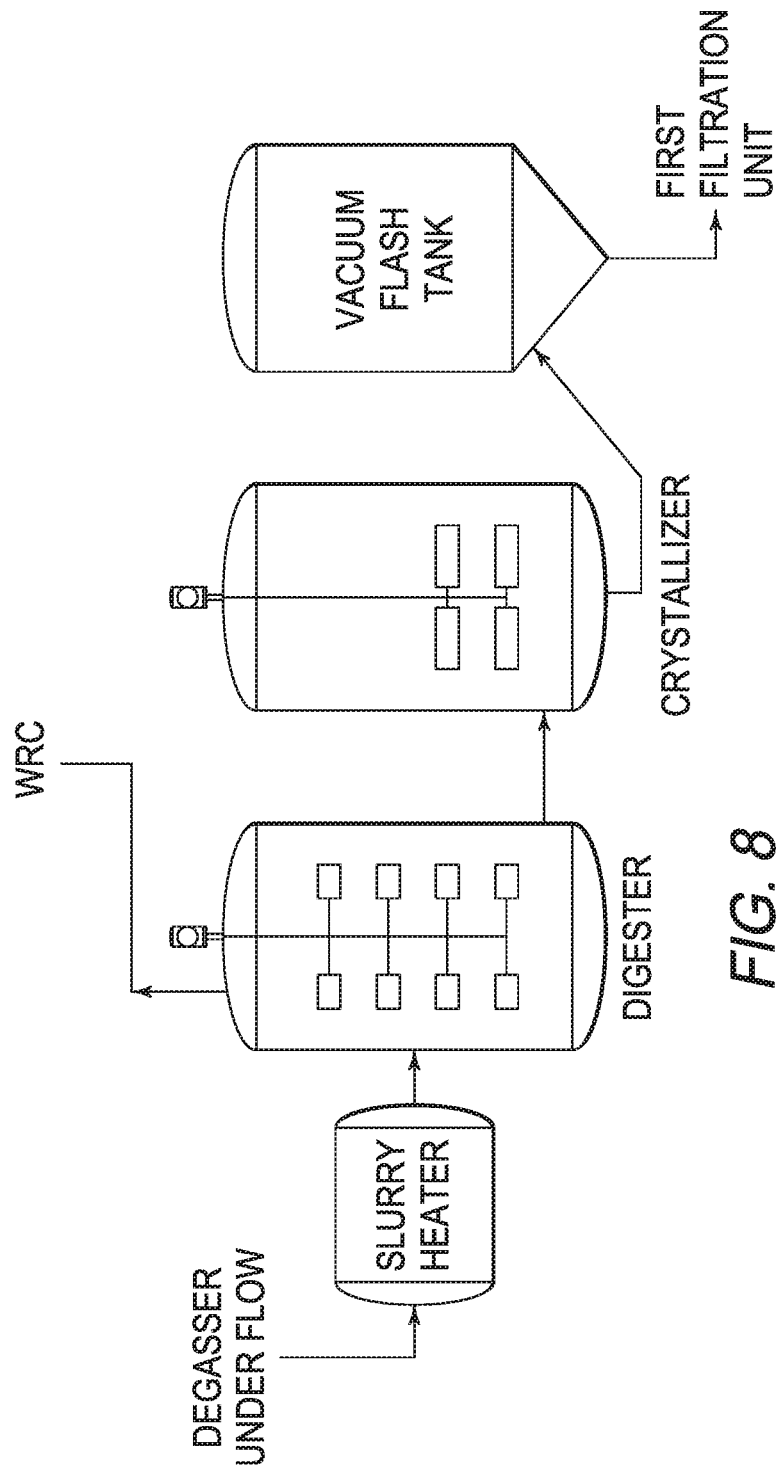
FIG. 8 shows a schematic diagrammatic arrangement of the Digestion unit according to one embodiment of the invention.

The digestion unit is shown schematically in FIG. 8.

As previously described the CTA of the underflow slurry obtained from the post oxidizer via the degasser unit contains moderately high levels of impurities which may be reacted via further oxidation to produce terephthalic acid. The post oxidizer slurry from the degassing unit may be at a temperature of from 125 to 200° C., preferably 140 to 180° C. and most preferably from 150 to 170° C. In order to partially dissolve the CTA crystals the slurry may be heated to a temperature of from 180 to 240° C., preferably 190 to 220° C., and most preferably 200 to 216° C. One heater is shown in FIG. 8. However, one of skill in the art will recognize that a series of heaters may be employed at this stage.

The heated post oxidizer slurry underflow may be pumped to a digestion unit as indicated in FIG. 8. At the elevated temperature in the digester partially oxidized products of p-xylene (p-toluic acid and 4-CBA) may be oxidized to terephthalic acid resulting in a more complete conversion of p-xylene to PTA. The primary obstacle toward achieving high conversion of p-xylene to PTA is mass transfer limitations associated with oxygen diffusion to embedded 4-CBA and p-toluic acid in the terephthalic acid. To achieve greater than 99% conversion requires overcoming these mass transfer limitations. This may be accomplished by operating the digester unit within the temperature range of 180 to 240° C. as previously described and at a pressure of from 790 to 2515 KPa.

According to the embodiments of the present invention compressed air is not supplied to the digesters in order to complete the oxidation digestion process. This is contrary to conventional digestion systems where oxygen in some form is injected directly into the digestion reactor. The inventors have surprisingly discovered that under the control of the present invention as described above, sufficient residual oxygen is retained in the post oxidizer slurry underflow to drive the oxidation to terephthalic acid by control of temperature and pressure within the digestion reactors. The digester reactor(s) may be equipped with an agitation system, comprised of several shaft-mounted blades on a steady bearing mounted shaft in order to provide sufficient agitation to the slurry.

Off-gases from the digester unit may be routed to the WRC for water removal, acid recovery and capture utilization of the thermal energy present as previously described.

Following treatment in the digester unit, the slurry may be transferred to a crystallization tank (crystallizer) where temperature is lowered to a range between 130 to 200° C., preferably 150 to 180° C. and most preferably 160 to 170° C. The crystallizer may be agitated to maintain solids suspension with agitator.

The off-gas from the crystallizer may be sent to a heat exchange heater in order to heat the steam which heats the post oxidizer slurry underflow enroute to the digestion unit. Such thermal energy control to prepare steam may be accomplished by a mechanical vapor recompression system, the mechanics of which are generally known to one of skill in the art. This energy recapture is not indicated in FIG. 8.

Following treatment in the crystallization unit, the slurry may be transferred to a flash cooling system including a vacuum flash tank (VFT). In the flash cooling system controlled cooling of the slurry product from the crystallization unit is conducted to avoid plugging of the system with solids.

The solids content of the slurry entering the flash cooling system may be from 20 to 60 wt. %, preferably, 25 to 50 wt. % and most preferably 30 to 40 wt. %.

In the flash tank, the temperature within the flash cooling system may be from 40 to 110° C., preferably 50 to 100° C., most preferably 60 to 90° C. Practically all insoluble material is precipitated or is crystallized from solution in the flash tank. The vapor generated in the flash tank may be routed to a condenser system wherein the remaining acetic acid may be recovered. Any remaining non-condensable gas may be removed from the system. The auxiliary equipment for the VFT is conventional equipment known to one of skill in the art and is not shown in FIG. 8.

The flash-cooled product slurry may be sent to the first filtration unit where the solids formed in the crystallizer are separated from the mother liquor in a rotary pressure filter. The filter is pressurized and constituted by multiple active zones. In the pressure filter the PTA is separated as a solid wet cake from the slurry. The filtrates collected from the rotary pressure filter described are sent to the filtrate tank of the materials supply unit.

As described in the preceding paragraphs, in the process according to the present invention thermal energy generated as a result of the exothermic oxidation reaction may be captured to generate mechanical energy to run at least the air compressor supplying compressed air to the primary and secondary oxidation reactors. Further the water content of the continuous oxidation and thus the reactivity and efficiency of the oxidation are controlled by removal of at least a portion of the water condensed from the water removal column off-gas.

Thus in the first embodiment, the present invention provides a continuous process to prepare an aromatic dicarboxylic acid, comprising:

oxidizing a di-alkyl substituted aromatic compound with compressed air in an acetic acid reaction medium in a primary bubble column reactor in the presence of a catalyst;

removing a portion of the three phase reaction medium containing catalyst from the primary bubble column reactor to a post-oxidation bubble column unit supplied with compressed air;

transferring the post oxidized reaction medium to a degassing unit and separating the post oxidation reaction medium to an overhead gas and an underflow slurry;

collecting an overhead gas from each of the primary oxidation reactor and the post-oxidation reactor with the overhead gas from the de-gassing unit and conducting the combined overhead gases to a water removal column;

transferring the underflow slurry from the de-gassing unit to a digestion unit comprising at least two digestion reaction tanks in series, wherein the temperature of the underflow slurry is increased to a temperature to at least partially dissolve precipitated solids and effect further oxidation of exposed intermediate oxidation products with air and catalyst present in the underflow slurry without addition of air to the digestion unit, to obtain a final oxidation slurry;

removing overhead gases from the digestion unit to the water removal column;

crystallizing the final oxidation slurry to obtain a filtration-ready slurry of the aromatic dicarboxylic acid;

filtering the filtration-ready slurry on a rotary pressure filter to obtain a mother liquor filtrate and a filtercake;

wherein the overhead gases sent to the water removal column are separated in the water removal column to an off gas comprising steam removed from the top of the column and an underflow liquid comprising acetic acid, at least a portion of the energy of the off gas comprising steam is collected and employed to drive an air compressor to supply the compressed air to the bubble column primary reactor and the post-oxidation bubble column unit, and a water content of the continuous oxidation is controlled by removal of water condensed from the water removal column off-gas.

In an aspect designated as the dry expander shown schematically in FIG. 5 the energy of the off gas comprising steam collected and employed to drive an air compressor may be obtained by passing the off-gas comprising steam from the water removal column through at least one heat exchange steam generator to employ thermal energy of the off-gas to produce process utility steam and a heat exchanged stream; collecting and removing condensed water from the heat exchanged stream to obtain a pressurized vapor stream; and sending the pressurized vapor stream to a gas expander to drive the air compressor.

In an aspect designated as the wet expander shown schematically in FIG. 7 the energy of the off gas comprising steam collected and employed to drive an air compressor may be obtained by superheating the off-gas comprising steam from the water removal column in at least one preheater; removing any; passing the superheated off-gas to a gas expander to drive the air compressor; and passing the expanded stream from the expander to at least one heat exchange steam generator to produce process utility steam and a heat exchanged stream; and collecting and removing condensed water from the heat exchanged stream.

As previously described in one aspect of the first embodiment, the di-alkyl substituted aromatic compound is paraxylene and the aromatic dicarboxylic acid is terephthalic acid.

As schematically shown in FIG. 9, in an aspect of the first embodiment, designated as the Brownfield aspect, the initial filtercake layer in the first filtration zone of the rotary pressure filter may be washed with multiple acetic acid washing operations to remove impurities and catalyst from the final product filtercake. The mother liquors containing catalyst from the filtration are collected and transferred to the filtrate tank in the materials unit. These liquors may optionally be passed through a filter such as a candle filter to remove solids before being sent to the filtrate tank. The washings may be followed with treatment in a hot nitrogen drying zone of the rotary pressure filter to at least partially remove acetic acid and water present in the filtercake. The rotary pressure filter is pressurized and contains multiple active filtration, wash and nitrogen feed zones. The filtercake may then be conveyed to a drying unit suitable for drying removal of acetic acid, such as, for example, a rotating hollow screw dryer, where it is heated with steam to evaporate substantially all the acetic acid from the cake as it is passes through the dryer. The vaporized acetic acid may be removed through a vent scrubber system as is conventional in the technology and the dried powder collected and transferred to the purification unit.

Figure 10:
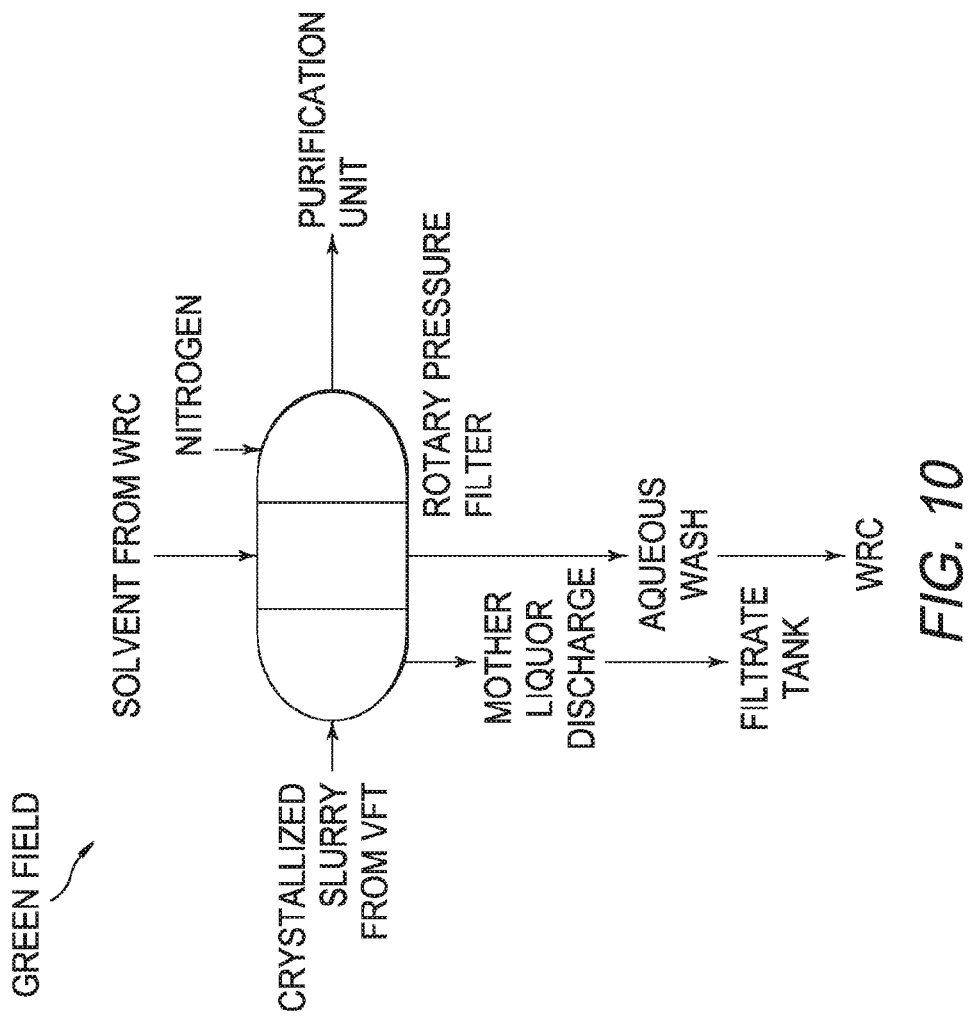
FIG. 10 shows a schematic diagrammatic arrangement of the First Filtration unit according to one embodiment of the invention (Greenfield).

A second embodiment of the continuous oxidation process, designated as the Greenfield embodiment is shown schematically in FIG. 10. According to this embodiment the flash-cooled product slurry from the VFT may be sent to the rotary pressure filter in the first filtration unit where the solids formed in the crystallizer are separated from the mother liquor in a rotary pressure filter. The filter is pressurized and constituted by multiple active zones. However, unlike the Brownfield aspect, in the Greenfield embodiment the initial filtercake in the first filtration zone of the rotary pressure filter after removal of the mother liquors is washed with hot water (90 to 100° C.) recovered from the oxidation overhead gases collected in the water removal column reflux tank. The water washed filtercake is then treated in a drying zone is provided for partially dewatering the cake with hot nitrogen gas that passes through the cloth to the cake. The water-washed partially dewatered filtercake is discharged from the pressure filter and directly conveyed to the purification unit without any further drying operation.

The mother liquor filtrates collected from the rotary pressure filter are sent to the filtrate tank, optionally being filtered to remove solids on the way to the filtrate tank. The wash waters collected from the rotary pressure filter are sent to the WRC.

As previously described the filtrate receivers and transfer lines are vented to a scrubber system.

Figure 11:
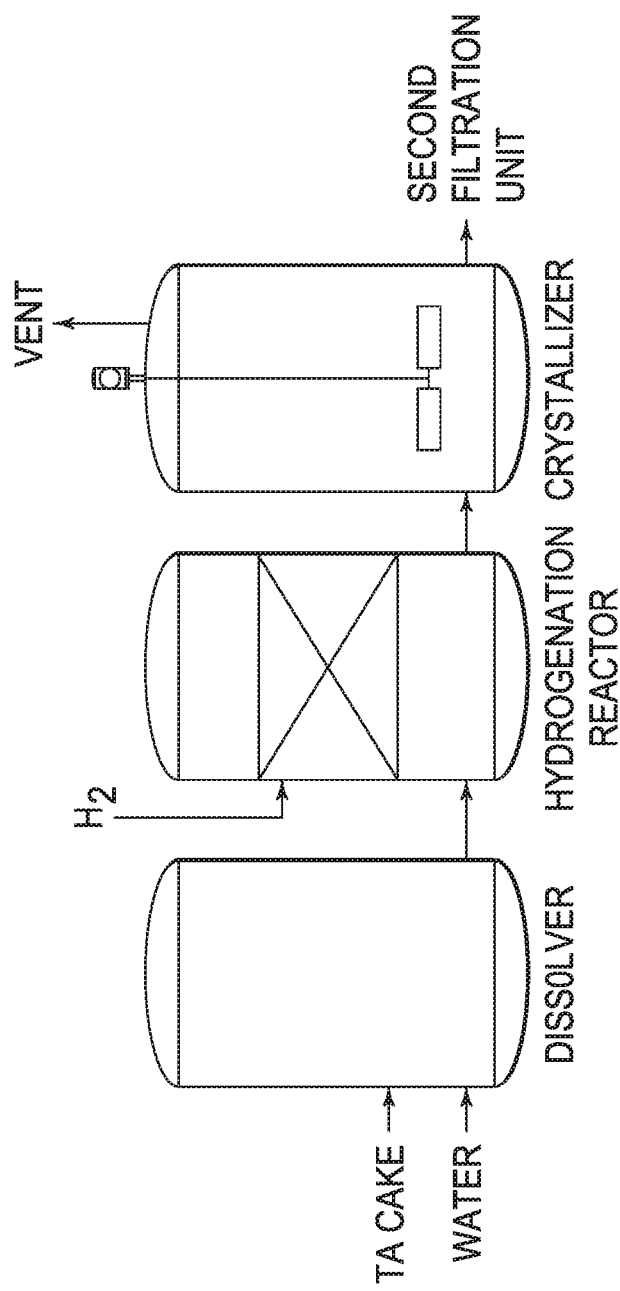
FIG. 11 shows a schematic diagrammatic arrangement of the Purification unit according to one embodiment of the invention.

FIG. 11 shows a schematic diagram of a purification unit which is utilized in both the Brownfield and Greenfield embodiments. In the Brownfield process the dried filtercake from the dryer is dissolved in the dissolver tank while in the Greenfield process the moist filtercake is dissolved in the dissolver. The two materials are designated generically as TA cake in FIG. 11. A conventional hydrogenation process may be employed, wherein the terephthalic cake is dissolved in water and the solution catalytically hydrogenated to convert retained impurities to more desirable and/or easily-separable compounds. The hydrogenation may be conducted at 280 to 290° C. where the terephthalic acid is in solution and the retained impurities available for reaction. Following the hydrogenation treatment the dissolved terephthalic acid may be selectively precipitated from the hydrogenated solution via multiple crystallization steps, and the resulting crystallization slurry sent to the second filtration unit for final isolation via filtration. One crystallizer is shown in FIG. 11, however, the number of crystallizers employed may be varied according to design and control parameters of the process. The control of crystallization in stages in multiple crystallization units may allow a step-wise temperature decrease in order to promote formation of particles of the product of a target size and distribution in the final crystallization slurry that is sent to the second filtration unit for isolation.

Figure 12:
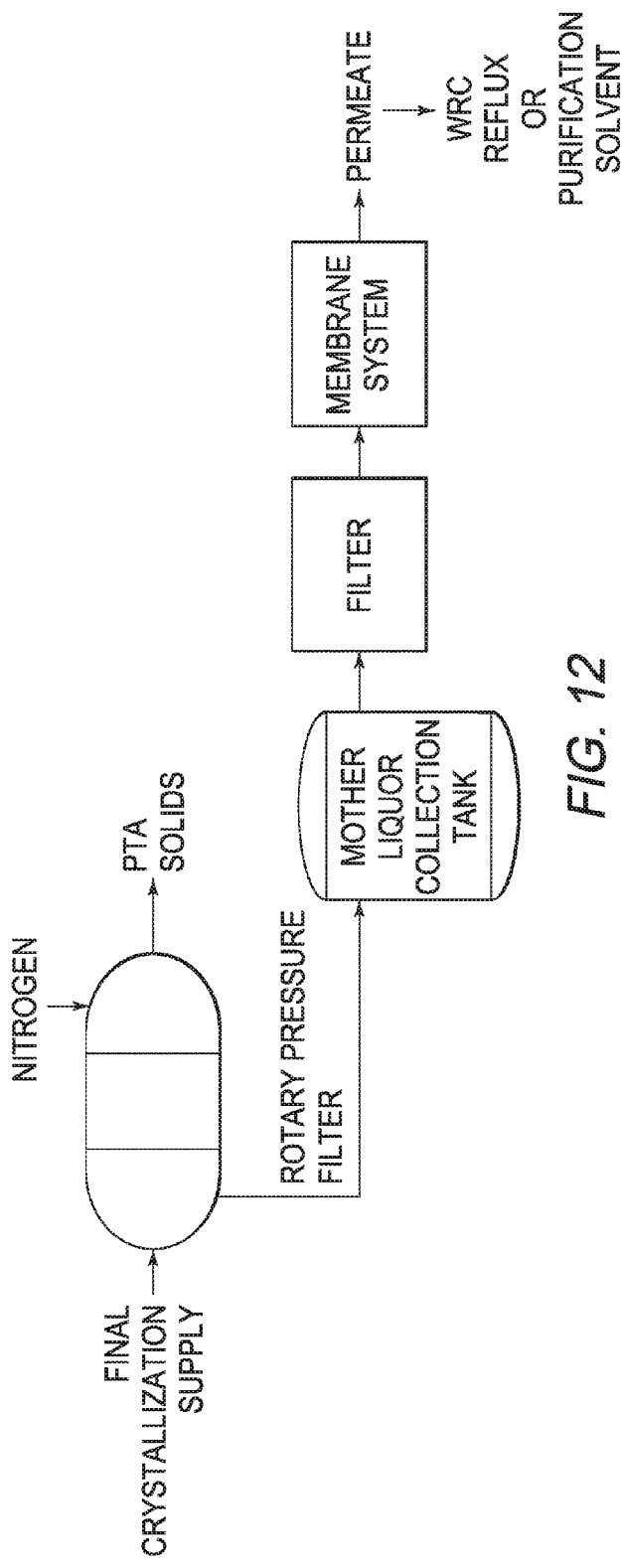
FIG. 12 shows a schematic diagrammatic arrangement of the Second Filtration unit according to one embodiment of the invention.

FIG. 12 shows a schematic drawing of the second filtration unit. The final crystallization terephthalic acid slurry may be filtered on a rotary pressure filter to separate the crystalline PTA from the filtrate. The various zones of the rotary pressure filter may be operated as previously described for the rotary pressure filter of the first filtration unit. The filtercake may be washed and then blown with hot nitrogen to remove retained water before being discharged for utility in further synthesis. The mother liquor filtrate is collected and then passed through a filter to remove any solids which passed the filter and then treated in a membrane system to obtain a water permeate which may be returned to the water removal column as reflux liquid.

As described above both the Brownfield and Greenfield embodiments offer significant reduction of process energy requirement by harvesting the exothermic energy generated in the oxidation reaction through steam generation and controlled expansion of the overhead vapors to drive the compressor train. Additionally, the water utilization is significantly conserved by recycle of aqueous condensates and filtrates to the WRC as described above. Further by control of process water content at the WRC the efficiency of the oxidation process as well as the quality and yield of product may significantly be improved.

The Greenfield embodiment offers not only the energy saving and water conservation of the Brownfield embodiment but also the added energy saving obtained by elimination of the energy consuming drying operation of the CTA presscake to remove acetic acid. Further the capital cost and operational costs of the drying unit are eliminated. Both embodiments provide the advantage of bubble column reactors over CSTR reactors in terms of energy savings and maintenance requirements.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. The schematic drawings shown in the Figures show the organization and arrangement of the major equipment utilized in the various embodiments. However, one of ordinary skill in the art recognizes that further ancillary and support equipment would be necessary in an actual operational system. Such functional equipment in support of the units shown is within the scope of the embodiments of the present invention. In this regard, certain embodiments within the invention may not show every benefit of the invention, considered broadly.

The invention claimed is:

1. A continuous process to prepare an aromatic dicarboxylic acid, comprising:
   oxidizing a di-alkyl substituted aromatic compound with compressed air in an acetic acid reaction medium in a primary bubble column reactor in the presence of a catalyst to obtain a three phase reaction medium;
   removing a portion of the three phase reaction medium containing catalyst from the primary bubble column reactor to a post-oxidation bubble column unit supplied with compressed air to obtain a post oxidized reaction medium;

transferring the post oxidized reaction medium to a de-gassing unit and separating the post oxidation reaction medium to an overhead gas and an underflow slurry;

collecting an overhead gas from each of the primary oxidation reactor and the post-oxidation reactor with the overhead gas from the de-gassing unit and conducting the combined overhead gases to a water removal column (WRC);

transferring the underflow slurry from the de-gassing unit to a digestion unit wherein the temperature of the underflow slurry is increased to a temperature to at least partially dissolve precipitated solids and effect further oxidation of exposed intermediate oxidation products with air and catalyst present in the underflow slurry without addition of air to the digestion unit, to obtain a final oxidation slurry;

removing overhead gases from the digestion unit to the water removal column;

crystallizing the final oxidation slurry to obtain a filtration-ready slurry of the aromatic dicarboxylic acid;

filtering the filtration-ready slurry on a rotary pressure filter to obtain a mother liquor filtrate and a filtercake; wherein the overhead gases sent to the water removal column are separated in the water removal column to an off gas comprising steam removed from the top of the column and an underflow liquid comprising acetic acid, at least a portion of the energy of the off gas comprising steam is collected and employed to drive an air compressor to supply the compressed air to the bubble column primary reactor and the post-oxidation bubble column unit, and the water content of the continuous oxidation is controlled by removal of water condensed from the water removal column off-gas.

2. The process of claim 1, further comprising:
passing the off-gas comprising steam from the water removal column through at least one heat exchange steam generator to employ thermal energy of the off-gas to produce process utility steam and a heat exchanged stream;
collecting and removing condensed water from the heat exchanged stream to obtain a pressurized vapor stream; and
sending the pressurized vapor stream to a gas expander to drive the air compressor.

3. The process of claim 2, wherein the condensed water from the heat exchanged stream is returned to the WRC or optionally removed as waste.

4. The process of claim 1, further comprising:
superheating the off-gas comprising steam from the water removal column;
passing the superheated off-gas to a gas expander to drive the air compressor; and
passing the expanded stream from the expander to at least one heat exchange steam generator to produce process utility steam and a heat exchanged stream; and
collecting and removing condensed water from the heat exchanged stream.

5. The process of claim 4, wherein the condensed water from the heat exchanged stream is returned to the WRC or optionally removed as waste.

6. The process of claim 1, further comprising:
washing the filtercake with acetic acid;
flowing nitrogen gas through the acetic acid washed filtercake to obtain a solid filtercake;
drying the solid filtercake to remove acetic acid;
reslurrying and purifying the dried filtercake of the aromatic dicarboxylic acid in an aqueous medium to obtain a purified dicarboxylic acid slurry;
filtering the purified aqueous slurry in a rotary pressure filter to obtain a final filtercake of the aromatic dicarboxylic acid and an aqueous mother liquor filtrate;
membrane filtering the aqueous mother liquor filtrate to obtain a water permeate; and
transferring the water permeate to the water removal column as water reflux.

7. The process of claim 6 wherein the acetic acid of the filtercake washing comprises acetic acid from the underflow liquid of the WRC.

8. The process of claim 6, wherein reslurrying and purifying the dried filtercake of the dicarboxylic acid comprises:
reslurrying the dried filtercake of the aromatic dicarboxylic acid in an aqueous medium;
treating the aqueous slurry with hydrogen in the presence of a hydrogenation catalyst to obtain a crystallization ready aromatic dicarboxylic acid slurry;
crystallizing the aromatic dicarboxylic acid in a series of at least two crystallization units;
filtering the crystallized aqueous slurry in a rotary pressure filter to obtain the final filtercake of the aromatic dicarboxylic acid and the aqueous mother liquor filtrate.

9. The process of claim 8, wherein water of the reslurry aqueous medium is obtained from the condensate of the overhead vapors from the WRC.

10. The process of claim 1, further comprising:
washing the filtercake with water to remove acetic acid and catalyst;
flowing nitrogen gas through the water washed filtercake to obtain a solid filtercake;
reslurrying and purifying the solid filtercake of the aromatic dicarboxylic acid in an aqueous medium to obtain purified aromatic dicarboxylic acid slurry;
filtering the purified aqueous slurry in a rotary pressure filter to obtain a final filtercake of the aromatic dicarboxylic acid and an aqueous mother liquor filtrate;
membrane filtering the aqueous mother liquor filtrate to obtain a water permeate; and
transferring the water permeate to the water removal column.

11. The process of claim 10, wherein reslurrying and purifying the dried filtercake of the dicarboxylic acid comprises:
reslurrying the solid filtercake of the aromatic dicarboxylic acid in an aqueous medium;
treating the aqueous slurry with hydrogen in the presence of a hydrogenation catalyst to obtain crystallization ready aromatic dicarboxylic acid slurry;
crystallizing the aromatic dicarboxylic acid in a series of at least two crystallization units;
filtering the crystallized aqueous slurry in a rotary pressure filter to obtain the final filtercake of the aromatic dicarboxylic acid and the aqueous mother liquor filtrate.

12. The process of claim 11, wherein water of the reslurry aqueous medium is obtained from the condensate of the overhead vapors from the WRC.

13. The process of claim 10, wherein the water for washing of the filtercake is water obtained from condensation of the overhead vapors from the WRC.

14. The process of claim 1 wherein the di-alkyl substituted aromatic compound is para-xylene and the aromatic dicarboxylic acid is terephthalic acid.

\* \* \* \* \*